United States Patent [19]

Ohara

[11] 4,280,551
[45] Jul. 28, 1981

[54] CENTRIFUGAL CASTING APPARATUS FOR DENTISTRY

[76] Inventor: Isao Ohara, 24-4, Midorigaoka 4-chome, Toyonaka, Osaka, Japan

[21] Appl. No.: 65,102

[22] Filed: Aug. 9, 1979

[30] Foreign Application Priority Data

Aug. 11, 1978 [JP] Japan .................... 53-98470

[51] Int. Cl.³ ............... B22D 13/06; B22D 13/10
[52] U.S. Cl. ..................... 164/287; 141/34; 164/289; 425/425
[58] Field of Search ............... 164/287, 289, 286, 114, 164/116, 336; 425/425; 141/34; 264/311

[56] References Cited

U.S. PATENT DOCUMENTS

| 1,457,040 | 5/1923 | McManus | 164/289 X |
| 2,451,103 | 10/1948 | Loew | 164/287 |
| 2,992,463 | 7/1961 | Berger | 164/287 X |
| 3,559,718 | 2/1971 | Hitchings | 164/289 X |

FOREIGN PATENT DOCUMENTS

| 678260 | 1/1964 | Canada | 164/114 |
| 790493 | 7/1968 | Canada | 425/425 |
| 2511349 | 9/1975 | Fed. Rep. of Germany | 164/289 |

Primary Examiner—Robert D. Baldwin
Assistant Examiner—Gus T. Hampilos
Attorney, Agent, or Firm—Armstrong, Nikaido, Marmelstein & Kubovcik

[57] ABSTRACT

A centrifugal casting apparatus for dentistry comprises a rotating member or platform for the mold having a mold disposed on one side thereof, a rotating member for the crucible movably positioned at the center of revolution of the said rotating member for the mold and provided with a crucible and a melting means, and a driving mechanism therefor, whereby metal for dentistry uses charged into the crucible is heated to be molten, while the mold is caused to rotate about the periphery of the crucible by means of the rotating member for the mold, and, after melting of the metal for dentistry uses is completed, the rotating member for the crucible is brought into engagement with the rotating member for the mold for rotation therewith where the metal in the molten state is cast from the crucible into the mold through impact force produced upon transmission of rotation as well as centrifugal force after initiation of rotation.

8 Claims, 10 Drawing Figures

CENTRIFUGAL CASTING APPARATUS FOR DENTISTRY

BACKGROUND OF THE INVENTION

1. Field of the Invention

The present invention relates to a centrifugal casting appratus for dentistry, which is useful in the production of metal products for dentistry such as gold crowns and dental plates.

2. Description of the Prior Art

Conventionally available among apparatus for casting metal products for dentistry such as gold crowns and dental plates has been a centrifugal casting apparatus which serves to cast molten metal from a crucible into a mold on a turntable rotating in the horizontal plane.

In such a centrifugal casting apparatus, metal is molten by a melting means such as an arc-heating one, and a crucible with the molten metal is allowed to rotate together with a mold thereby cast the molten metal from the crucible into the mold by centrifugal force, whereby two major problems have been encountered; one is the oxidation of the molten metal surface attributed to its contacting with oxygen in the air during a prolonged period of time required for casting, and the other involving solidification without allowing molten metal to fill sufficiently into the extremities of mold cavities because of a lack of centrifugal force in the initial stage of casting. In other words, these problems are attributed to the fact that after metal is completely molten, it requires several seconds since initiation of rotation to produce a high rate of rotation enough to obtain centrifugal force of the magnitude for casting. This has led to the finding that these problems may be able to be solved if great centrifugal force which enables casting can be imparted immediately upon melting of metal for dentistry.

The centrifugal casting apparatus conventionally utilized have a crucible, a mold, etc. disposed on a turntable revolving in the horizontal plane and have to be allowed the level area of a determined size necessary to insure the rotation thereof, resulting in a increased dimension of frames of the apparatus and bringing about difficulties in observing or inspecting a state of metal melting in the crucible from the outside. And, it is strongly desired to improve and eliminate these problems.

SUMMARY OF THE INVENTION

The present invention has been completed with a specific view to solving these problems encountered so far. It is the primary object of the present invention to impart sufficiently great centrifugal force to molten metal from the very beginning of casting of molten metal, and a further object of the present invention is to provide a centrifugal casting apparatus for dentistry capable of imparting centrifugal force varying with the stages of casting or according to pouring of molten metal and pressing it after being poured.

It is another object of the present invention to provide a centrifugal casting apparatus of a tilting type with a reduced volume of revolution required to impart centrifugal force.

It is further another object of the present invention to provide an optimal-shaped crucible for use in the centrifugal casting apparatus.

Still further objects of the present invention are to be indicated by the following detailed description, claims and drawings accompanied whereby illustrated below are disclosures of the basic concept of the present invention and the best mode of the embodiment thereof, and it is to be expressly understood that the present invention is not limited thereto.

DESCRIPTION OF PREFERRED EMBODIMENTS

The basic construction of the apparatus according to the present invention consists of a rotating member or platform for the mold having a mold and a balance weight disposed on opposite sides thereof, and a hole for movable fitting provided on the center; a driving mechanism capable of revolving the rotating member for the mold; a rotating member for the crucible being positioned in loose engagement with the said rotating member for the mold through the hole for movable fitting and having a crucible mounted; a loading and unloading mechanism for transmitting the rotation of the rotating member for the mold to the rotating member for the crucible; and a melting means for melting metal charged into the crucible. The present invention is illustrated below in detail based on the example for embodiment as shown in the drawings.

The present invention can be carried out into practice in either of a horizontal type with the rotating members revolving horizontally and a vertical type with those revolving vertically. As an example for embodiment is mentioned a tilting type, an intermediary type of the two types described above, with the rotating members revolving in an inclined position. The tilting type centrifugal casting apparatus, with its oblique surface of revolution, has the characteristic advantage over the horizontal and vertical type in terms of a reduced size and an improved handling of the apparatus. According to the kind of means of heating for melting metal charged into a crucible, the casting apparatus is classified into an arc type, gas type, high-frequency type, etc. The present invention may be carried into practice in any heating method out of these, and in an example for embodiment is illustrated an argon-arc type in which heating by an electric arc is effected under an atmosphere of argon gas.

Figure 1:
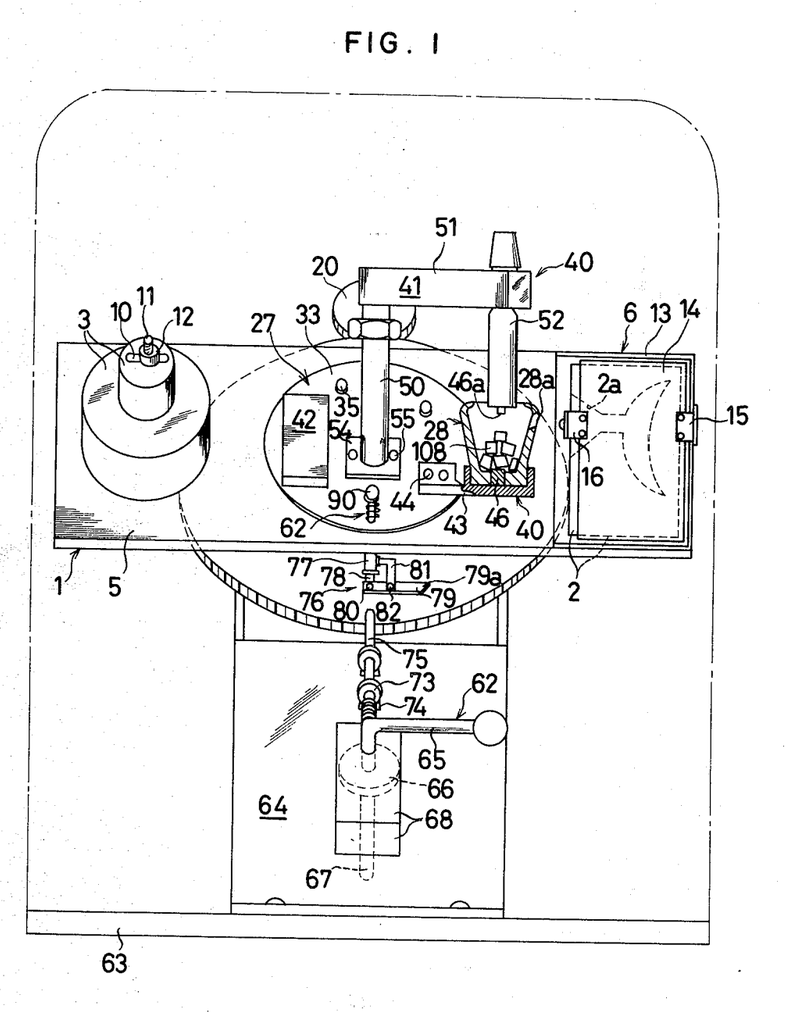
FIG. 1 is an elevational view of a casting apparatus in accordance with the present invention, with a view, partly in section, of the portion surrounding the crucible.
Figure 2:
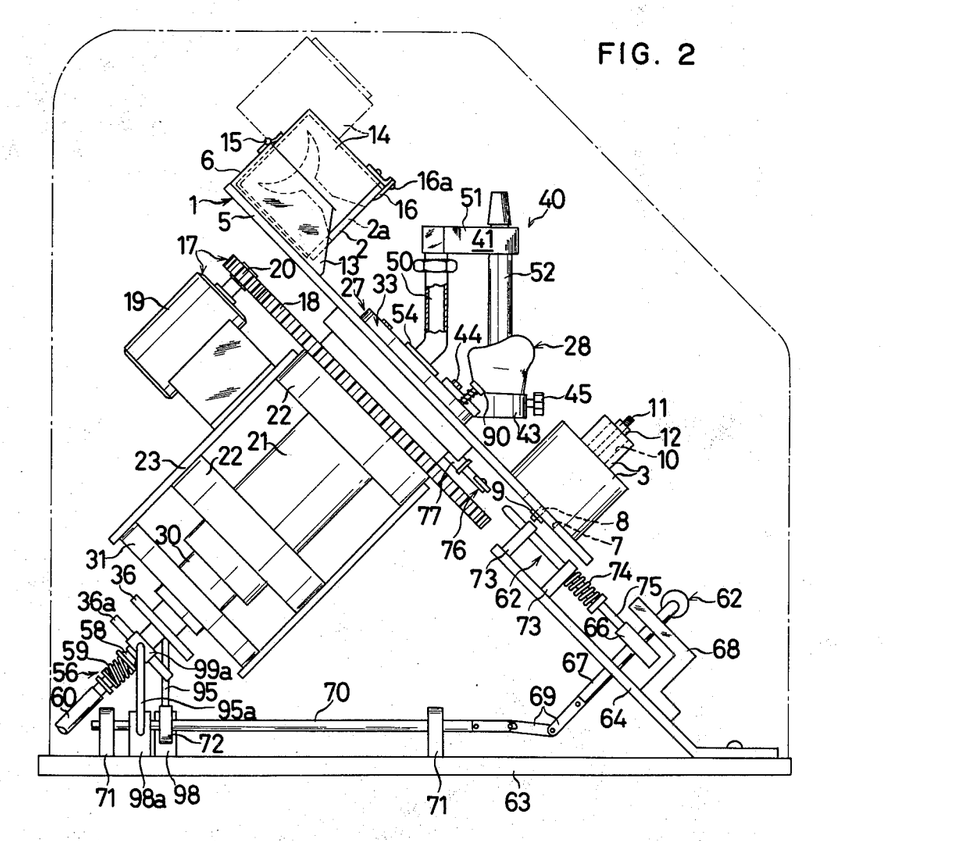
FIG. 2 is a side view of FIG. 1 after revolving the rotating member for the mold as shown in FIG. 1 counterclockwise by 90°.
Figure 3:
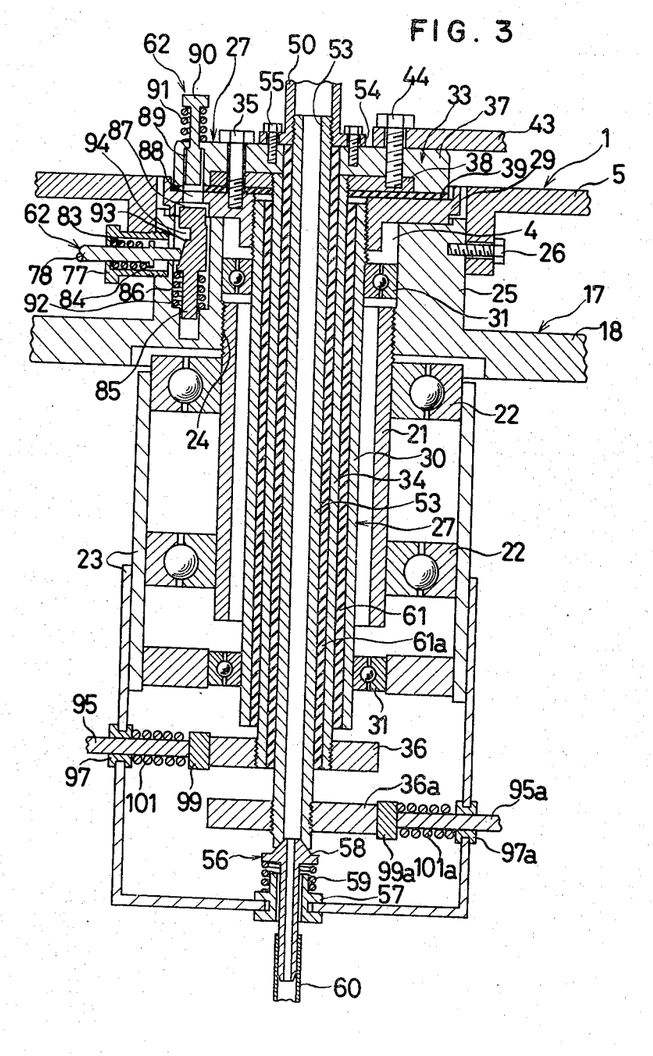
FIG. 3 is a view, partly in longitudinal section, of the main part of the casting apparatus.

FIG. 1 is a front view of the apparatus in accordance with the present invention showing a casing part schematically in the phantom lines, FIG. 2 being a side view thereof, and FIG. 3 is a partially longitudinal sectional view of the main part of the apparatus, whereby in FIG. 2 for convenience's sake of drawings, there are shown the position and condition of the rotating member for the mold after revolving counterclockwise by 90° from those shown in FIG. 1.

Rotating member or platform for the mold 1 has a mold 2 disposed on one side and a balance weight 3 on the other side, and is provided on the center with a hole for movable fitting 4 adapted to fit and position a rotating member for the crucible 27 as hereinafter described in a way of loose engagement. Illustrated as an example of embodiment is a square-shaped plate or platform 5 having a two-component balance weight comprising the larger and smaller ones 3 and 3 disposed on one side thereof, and a mold 2 received in a casing for mold 6 being placed on the other side in an inclined position.

So as to mount the balance weight 3 on the square-shaped plate 5, a long groove 7 is provided through drilling on the square-shaped plate 5 and a threaded bar 8 is disposed in a projecting way on the bottom surface of a lower balance weight, whereby the said threaded bar 8 is inserted through the long groove 7 to an appropriate position thereof for fixing by a locknut 9. Through a long groove 10 provided by drilling on the upper balance weight 3 is also inserted a threaded bar 11 disposed in a projecting way on the surface of the lower balance weight 3 to thus be fixed by a locknut 12. Consequently, the upper and lower balance weights 3 and 3 can be allowed to travel by a determined length or distance relative to the square-shaped plate 5 for being fixed therewith to thereby adjust the revolution balance in accordance with the weight of the mold 2.

Casing for the mold 6 consists of an inner case 14 being rotatably mounted on an outer case 13 by hinge 15, etc., to fit the mold 2 into the inner case 14, whereby a flow-in portion for metal 2a is adapted to be turned to the inside of the square-shaped plate 5 on the occasion of casting of molten metal, and after casting is completed, the inner case is revolved as shown in FIG. 2 in the phantom lines so that the mold 2 may be able to be taken out easily. Numeral 16 designates a stopper serving to keep the mold 2 from coming out of the inner case 14, and it is adapted to be rotated around a pin shaft 16a.

Driving mechanism 17 is disposed, aiming at rotating the said totating member for the mold 1, and shown as an example of embodiment is a rotating gear 18 connected on the under-surface of the square-shaped plate 5 of the rotating member for the mold, whereby the said rotating gear 18 is adapted to be rotated by a motor 19 and a pinion 20 for reducing appropriately a rotation speed of the motor 19.

The rotating gear 18 is supported by a hollow shaft pipe for the gear 21 mounted thereunder through screwing, etc. and supported further by a support frame for fixing 23 through bearings 22 and 22 placed vertically in the upper and lower positions so that the hollow shaft pipe for the gear 21 may be rotated freely, but fixed in the axial direction, as the rotating gear 18 is rotated.

For connection of the square-shaped plate 5 with the rotating gear 18, a through bore 24, is provided on the central part of the rotating gear 18, and an annular wall 25 is formed vertically on the circumference of the through bore 24 to mount the square-shaped plate 5 on the upper part of the annular wall 25, by fixing with a bolt 26, etc. an engaging shaft 85 is positioned internally within the annular wall 25 and forms a part of the loading and unloading mechanism 62, as hereinafter described, when the square-shaped plate 5 is kept secured to the rotating gear 18, the hole for movable fitting 4 of the square-shaped plate 5 remains in communication with the hollow shaft pipe for the gear 21.

The rotating member for the crucible 27 is positioned in loose engagement with the hole movable fitting 4 of the rotating member for the mold 1, and has a crucible 28, placed on the upper surface. Shown in an embodiment is a rotating member for the crucible of the construction being below described so as to hold the rotating member for the crucible 27 in loose engagement and perform efficient supply of gas and electric power for argon arc heating.

This is to say; so as to form a part of the rotating member for the crucible 27, a hollow shaft pipe for the saucer 30 is mounted by screwing, etc. on the central part of the under surface of a saucer 29 having such a diameter as may be able to engage the hole for movable fitting of the square-shaped plate 5 in the said rotating member for the mold 1 and inserted into the said hollow shaft pipe for the gear 21 at a fixed distance spaced between them, whereupon the upper part of the hollow shaft pipe for the saucer 30 is held by bearing 31 fixed on inner circumferential wall of the said annular wall 25, and the lower part thereof is projected out of the hollow shaft pipe for the gear and supported by bearing 31 mounted on the support frame for housing 23 so that it may be fixed along the axial direction and rotated freely. At the same time, the saucer 29 is kept placed on the surface of the annular wall 25.

On the other hand, a hollow shaft pipe for the disc body 34 is attached by screwing, etc. on the under surface of a disc body 33 provided on the central part with a through bore 32. The hollow shaft pipe for the disc body 34 is inserted into the said hollow shaft pipe for the saucer 30 from above to place the disc body on the saucer 29, followed by securing by bolts 35, etc. the disc body 33 to the saucer 29 to one piece, while the hollow shaft pipe for the disc body 34 is allowed to project at its lower part out of the hollow shaft pipe for the saucer 30 to thereby mount the electrode disc made of metal 36 at the projected end by screwing, etc.

Consequently, the disc body 33 and the hollow shaft pipe for the disc body 34 are adapted to be rotated in one piece when the saucer 29 and the hollow shaft pipe for the saucer 30 revolve.

Construction of the disc body 33 itself, taking into consideration the electric system, is composed of insulating disc material 37, conductive small disc material 38 and insulating lower disc material 39, whereby the insulating disc material 37 is placed in such a way as it may cover the surface and sides of the conductive, small disc material 37 and its bottom surface is fitted with the insulating lower disc material 39.

Mounted on the rotating member for the crucible 27 are the said crucible 28, a torch part 41 constituting a part of a heating means 40 fixed to the rotating member for the crucible 27 or other portion for connection thereof with the said crucible 28, and a small balance weight 42.

So as to mount the crucible 28, metal-made, conductive attachment bed for the crucible 43 is screwed by the bolt 44 passing through the insulating disc material 37 down to the conductive small disc material 38 placed thereunder. On the attachment bed for the crucible 43 is placed the crucible 28, whereupon the crucible 28 is fixed by a fixing screw 45. Within the bottom of the crucible 28 is placed an electrode rod for generating arc 46, and the electrode rod 46 is in direct contact with the attachment bed for the crucible 43.

The position and condition for fixing the crucible 28 is to be so set as the crucible 28 may retain the vertical condition when the crucible 28 is located at a fixed position or when it, in an embodiment, is located at the most right side as shown in FIG. 1 supposing that the rotating member for the crucible 27 in the inclined state is rotated counterclockwise. Once such fixing position and condition are set, the crucible 28 is brought into the non-vertical state due to the inclined condition of the rotating member for the crucible 27 mounted with the crucible 28, when it revolves and moves to other position, or any position other than the most right side.

The small balance weight 42 is placed for fixing on the rotating member for the crucible 27 existing on the opposing side of the crucible 28 so as to counterbalance the crucible during rotation.

Figure 7:
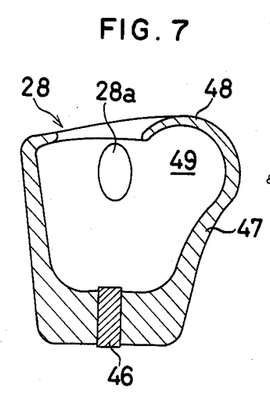
FIG. 7 is a central, sectional view of a crucible.

The form and shape of the crucible 28 itself may be of any of the conventional ones for utilization, and illustrated in an example for embodiment is a crucible 28 with the wall 47 being warped on its upper part to form a hood 48 and a small chamber 49 whereby the inner surface extending from the small chamber 49 to a pouring portion for molten metal 28a formed on one side of the crucible 28 is made to a smooth, curved surface free from roughness. When the crucible of such a form and shape is utilized, molten metal is prevented from overflowing out of the crucible 28 by means of the hood 48, even if the crucible 28 is brought into a rapid rotation in an impact causing way from the very beginning, and the molten metal is permitted to flow out smoothly through the flow-in portion for molten metal 28a by taking advantage of the initial impact force.

The construction of the torch part 41 connected with the crucible 28 as shown in an example for embodiment is roughly the same as the one used conventionally for the argon arc type, and comprises of hood 52 while hanging down into the crucible 28 being attached to the arm 51 mounted on the support 50 and the electrode rod 46a being placed inside the hood 52 whereby argon gas is allowed to blow out from the hood 51 toward the crucible 28 to generate arc between the electrode rod 46a within the hood 52 and the electrode rod 46 within the crucible 28.

The torch part 41 as shown in an example for embodiment has a hollow inside and utilizes a conductive, metal-made support 50, together with electrical wiring conducted between the support 50 and the electrode rod 46a for electric communication which is not illustrated.

In order to mount the support 50 on the rotating member for the crucible 27, a hollow shaft pipe for the torch part is attached to the lower part of the support 50 by screwing, etc., and the said hollow shaft pipe for the torch part 53 is inserted into the said hollow shaft pipe for the disc body 54, while a flange part of the support 54 is secured for mounting by the bolt 55 to the insulating disc material 37. In this case, the lower part of the hollow shaft pipe for the torch part 53 is left projecting out of the hollow shaft pipe for disc body 34, and attached to the projected end is the electrode disc 36a by screwing, etc.

Furthermore, fitted into the lower, opening end of the hollow shaft pipe for the torch part is the gas piping fixture made of insulating material 56 for supplying gas. By this, the torch body 57 is secured to the support frame for fixing 23, while the sliding tip pipe 58 is inserted through the said torch body 57, to thereby allow its tip end to fit in the lower, opening end of the hollow shaft pipe for the torch part 53 resiliently by means of a spring 59 inserted into the torch body 57. The numeral 60 designates a gas supply pipe.

So as to insure reasonably spacing and electric insulation between each two of shafts, cylindrical-shaped insulation sleeves of an appropriate thickness 61 and 61a are outwardly inserted into the hollow shaft pipe for the disc body 34 and the hollow shaft pipe for the torch part 53 as occasion demands.

The loading and unloading mechanism 62 serves to transmit the rotation of the rotating member for the mold 1 to the rotating member for the crucible 27 in loose engagement, and is adapted to rotate both of them in one piece and oppose the flow-out portion for molten metal 28a of the crucible 28 to the flow-in portion for molten metal 2a of the mold 2 while they are interengaged and kept rotating in one piece. Illustrated in an example for embodiment is the one capable of performing the above mentioned loading and unloading function as well as switching on and off the argon gas and electric current for arc being fed.

The loading and unloading mechanism 62 as shown in the embodiment consists of a tilting plate 64 fixed at the front position of a base platform for fixing 63, and a control shaft 67 equipped with a handle shaft 65 and firmly provided with a cam 66 being inserted through the tilting plate 63 to support the control shaft 67 with a support means for the control shaft 68 for connection through a universal coupling 69 placed at the shaft bending position with a switching shaft 70 acting to switch on and off the electrode brush es 99 and 99a as hereinafter described. The switching shaft 70 is supported in the horizontal plane on the base platform for fixing 63 by means of bearings 71 and 71, and equipped on the rear part with two cams 72 and 72a.

Placed in front of the control shaft 67 of the tilting plate 64 is a thrusting shaft 75 supported with the bearings 73 and 73 and externally fitted with a spring 74 for pulling back, whereby the rear end portion of the thrusting shaft 75 is fitted resiliently to the cam 66 by force of the spring 74. The loading and unloading mechanism 62 as shown in the embodiment of the present invention is urged by operating of the handle shaft 65 to actuate the switching shaft 70 and the thrusting shaft 75 to perform transmission of the rotation from the rotating member for the mold 1 to the rotating member for the crucible 27 as well as switching on and off of the argon gas and electric current for the arc.

That is to say: referring to the mechanism for transmitting the rotation from the rotating member for the mold 1 to the rotating member for the crucible 27, the numeral 76 is a lever device mounted to the annular wall 25 of the rotating gear 18, which comprises a supporting sleeve 77 securedly provided on the annular wall 25 to insert a sliding shaft 78 in the said sliding sleeve 77 and mount rotatably a lever 79 by means of a supporting shaft 80 to one end of the said sliding shaft 78, and an L-shaped support element material 81 securedly provided on the outer surface of the supporting sleeve 77 to mount the end thereof rotatably by means of a supporting shaft 82 to the intermediary portion of the said lever 79. Consequently, when the end portion 79a of the lever 79 is moved up and down, the lever 79 gets in motion centering around the supporting shaft 80 in such a manner as a balance does, whereupon the end of the lever 79 at the supporting shaft 80 urges the sliding shaft to slide and travel within the supporting sleeve 77.

Further, the sliding shaft 78 has the spring 83 outwardly inserted inside the supporting sleeve 77 whereby one end of the spring 83 is fitted into the inner wall of the supporting sleeve 77 and the other one into the vertical wall 84 circumferentially provided on the sliding shaft 78 to thereby compress resiliently the sliding shaft 78 toward the inside of the annular wall 25.

Figures 5, 6:
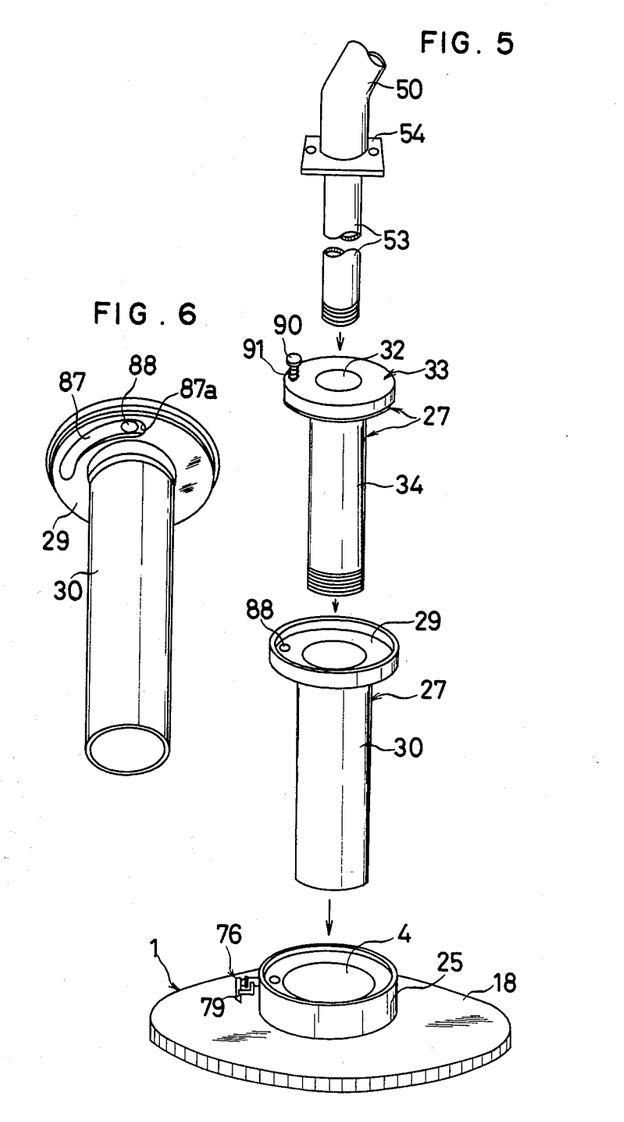
FIG. 5 is a disassembled arrangement of each of hollow shaft pipes.
FIG. 6 is a perspective view of a hollow shaft pipe for a saucer, looking obliquely from beneath the same.

On the other hand, within the annular wall 25 is provided a longitudinal hole 86 to permit insertion of an engaging shaft 85 of a roughly cylindrical form, and a tapered groove 87 having a length corresponding to about a quarter of the circumference as shown in FIG. 6 is formed on the under surface of the saucer 29, while a through bore 88 of a diameter enough to insert and remove the stopper pin as hereinafter described is provided at one end of the tapered groove 87 on the deepest position 87a.

In the vicinity of the circumferential end of the disc body 33 is also provided through drilling a hole for the stopper pin 89 being adapted to insert the stopper pin 90 therein so that the lower end of the stopper pin 90 may be, ordinarily, kept pulled up within the disc body 33 by means of a spring 91 externally inserted in the stopper pin 90.

The function of the engaging shaft 85 may be any kind of the ones capable of holding the temporary engagement with sliding shaft 78, keeping the whole engaging shaft 85 compressed inside the annular wall 25 during engagement but leaving the engaging shaft 85 moving upward by force of the spring 92 during disengagement. Illustrated in an example of embodiment is the one having a nearly cylindrical-shaped body tapered at the lower part to a smaller diameter to externally insert the spring 92, together with a inclined sliding surface 93 and an engaging concave portion 94 extending thereto being provided on the side wall part ranging from the central part of the nearly cylindrical-shaped body to the upper part.

The function of the stopper pin 90 is to compress the upper end of the engaging shaft 85 downward for movement so as to allow the said engaging shaft 85 to engage the sliding shaft 78. Normally, the stopper pin is positioned to be kept pulled up by force of the spring 91.

Indicated in FIG. 3 is the state where the upper end of the engaging shaft 85, after the engaging shaft 85 has been brought out of engagement with the top end of the sliding shaft 78, is projected out of the upper surface of the annular wall 25 to get into engagement with the tapered groove 87 of the saucer 29, thus engaging the saucer 29 of the rotating member for the crucible 27; on this occasion, the rotation of the rotating member for the mold 1 comes to be transmitted to the rotating member for the crucible 27.

Figure 4:
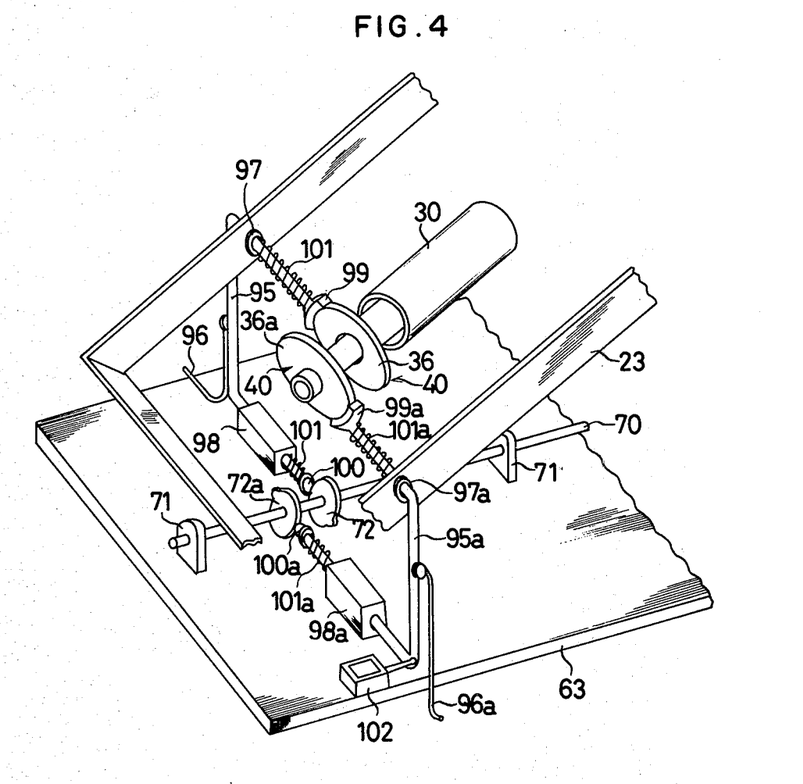
FIG. 4 is a schematic, perspective view of a switch mechanism for electrode discs, showing a partly broken away support frame for fixing.

The switching mechanism for electrode brushes, of which a simplified condition is shown in FIG. 4, comprises two pieces of nearly U-shaped brush frames 95 and 95a connected with electric wirings 96 and 96a being mutually opposed, the upper parts thereof being supported on the support frame 23 for fixing through insulating bushes 97 and 97a while the lower ones being inserted through insulating support means 98 and 98a placed on the base platform 63 for supporting therewith; the brushes 99 and 99a fitting into the electrode discs 36 and 36a being provided on the upper top ends of the brush frames 95 and 95a; the cam fitting portions 100 and 100a fitting into teh cams 72 and 72a securedly equipped in the switching shaft 70 being provided on the lower top ends thereof; and the springs 101 and 101a being inserted in the upper and lower arms of the brush frames 95 and 95a adapted to fit the brushes 99 and 99a and the cam fitting portions 100 and 100a resiliently with the electrode plates 36 and 36a and the cams 72 and 72a. The limit switch 102 acting to open and close solenoid valve (not indicated in the drawings) for supply of gas is fitted on the base platform for fixing 63, etc., and is fitted to the brush frame 95a, thus being adapted to utilize motion of the brush frame 95a for actuating it.

Figure 8:
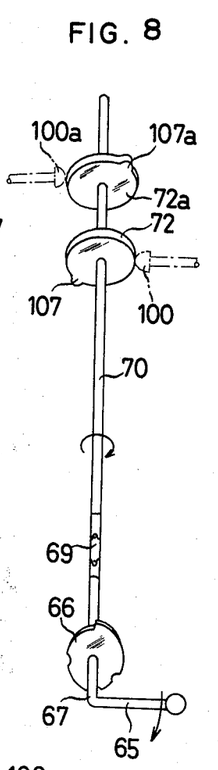
FIG. 8 is a schematic illustration of operation of a variety of cams.
Figure 9:
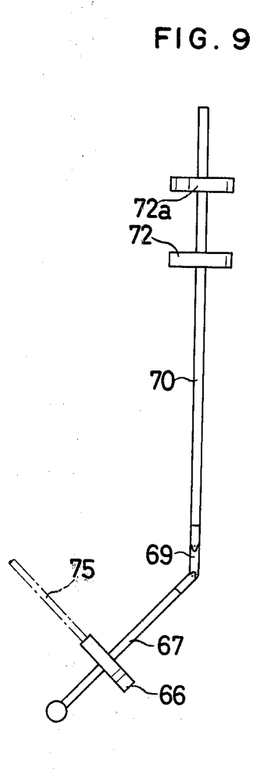
FIG. 9 is a side view of FIG. 8.
Figure 10:
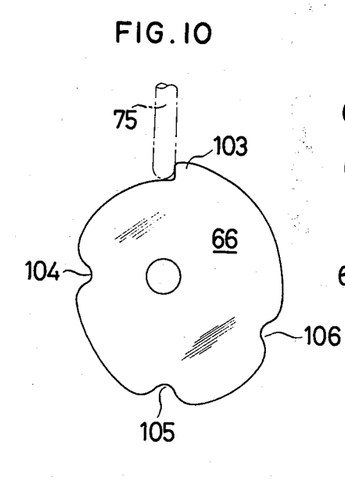
FIG. 10 is a front elevation of an operating shaft cam.

FIGS. 8 and 9 are schematic illustrations showing the operation of the cams 66 of the control shaft 67 and the cams 72 and 72a of the switching shaft 70, whereby the cam 66 of the control shaft 67 has an eccentric cam having a step portion 103, a concave portion for rotation of the mold 104, a concave portion for rotation of the crucible 105 and a concave portion for actuating the brush to open 106 formed, and the cams 72 and 72a of the switching shaft 70 is a circular-formed cam having protrusions 107 and 107a provided in a projecting way.

The handle shaft 65, initially, is to be so positioned as it may face sideways to the right as shown in FIGS. 1 and 8, whereby the thrusting shaft 75 is fitted into the step portion 103 of the cam 66.

When the handle shaft 65 is rotated by 90° clockwise, for example, the thrusting shaft 75 gets into engagement with the concave portion for rotation of the mold 104, wherein, by sensing the motion encompassing a revolution angle of 90° taking place in the course of this by means of a limit switch not indicated in the drawings, and by corresponding the said limit switch to a protrusion as not shown in the drawings to be provided on the under surface of the cam 66, the control shaft 67 or the switching shaft 70, the motor 19 operates to revolve the rotating member for the mold 1; the cams 72 and 72a of the switching shaft 70, being in the circualr form, are kept in engagement with the cam fitting portions 100 and 100a as they are, even when the switching shaft 70 is rotated by 90°.

When the handle shaft 65 is further rotated by 90°, the thrusting shaft 75 is brought into engagement with the concave portion for rotation of the crucible 105, whereupon, because the cam 66 is an eccentric cam, it urges the thrusting shaft 75 to thrust out a determined distance toward the lever device 76 in the front, and to act on the lever device 76, then revolving the rotating member for the crucible 27. At the time of this, the protrusions 107 and 107a on the cams 72 and 72a of the switching shaft 70 is not brought to be fitted into the cam fitting portions 100 and 100a, while the brushes 99 and 99a retain the engagement conditions as they are.

When the handle shaft 65 is rotated furthermore by 30° to 45°, the thrusting shaft 75 gets into engagement with the concave portion for actuating the brush to open 106, and the protrusions 107 and 107a on the cams 72 and 72a of the switching shaft 70, for the first time, come to be fitted into the cam fitting portions 100 and 100a to thereby push the cam fitting portions 100 and 100a away to the left and right sides, causing the brushes 99 and 99a of the brush frames 95 and 95a to get apart from the electrode discs 36 and 36a and resulting in interruption of supply of electric current.

As for the thrusting mechanism of the thrusting shaft 75 for actuating the lever device 76, the mechanism described above with the use of the cam 66 is illustrated as a mere example of an embodiment of the invention, and other mechanisms such as the ones utilizing gears and rack pinions are of course feasible; any type fo mechanisms may be employable, only if they function to thrust out the thrusting shaft 75 toward the lever device 76.

With the construction of the present invention being described above, and at the time when the preceding casting work has been completed, the engaging shaft 85 is held in engagement with the saucer 29 as indicated in FIG. 3, so that the rotation of the rotating member for the mold 1 remains in the position to be transmitted to the rotating member for the crucible 27. In carrying out casting work anew, therefore, it is necessary to release the engagement between the engaging shaft 85 and the saucer 29. For the reason of this, the stopper pin 90 is compressed downward manually by hand to fit the lower end of the stopper pin 90 on the upper end of the engaging shaft 85, thus compressing the engaging shaft 85 to move downward.

In accordance with downward movement of the eganging shaft 85, on the other hand, the top end of the sliding shaft 78 being fitted onto the inclined sliding surface of the engaging shaft 85 comes to slide and move on the inclined sliding surface 93 toward the engaging concave portion 94 for engagement therewith, thus bringing the sliding shaft 78 in engagement with the engaging shaft 85, whereby the whole engaging shaft 85 enters into the annular wall 25, and the saucer 29 of the rotating member for the crucible 27 gets into loose engagement with the rotating member for the mold 1.

In the lever device 76 at this time, the top end of the sliding shaft 78 engages the engaging concave portion 94, and the resulting force of the spring 83 urges the sliding shaft 78 to slide and move inside the supporting sleeve 77 toward the engaging shaft 85, whereupon the lever 79 is drawn at the supporting shaft 80 toward the engaging shaft 85 and positioned to be slightly rotated around the supporting shaft 82.

When the sliding shaft 78 is in engagement with the engaging shaft 85, the rotating member for the crucible 27 can be rotated by hand independently of the rotating member for the mole 1; in case the crucible 28 is positioned to be at the right-side end as shown in FIG. 1, the crucible 28 is held in the vertical plane, and, above it, the the electrode rod 46a of the torch part 41, vertically, gets opposed to the electrode rod 46 of the crucible 28. Both the hollow shaft pipe for the disc body 34 and the hollow shaft pipe for the torch part 53 in the rotating member for the crucible 27 is adequately fitted to the brushes 99 and 99a at their respective electrode discs 36 and 36a by force of the springs 101 and 101a, to apply the brake of a certain magnitude, thus preventing the rotating member for the crucible 27 from revolving freely and spontaneously by the weight of the crucible 28, etc.

After setting of the position for the crucible 28 is completed, metal for dentistry 108 is charged into the crucible 28, and a switch for a power source and a knob for a gas pipe not indicated in the drawings are turned on to energize the small disc material 38 by way of one system for electric current for arc from the brush frame 95 connected with electrical wiring 96 through the brush 99, the electrode disc 36 and the hollow shaft pipe for the disc body 34, and to further energize therefrom the electrode rod 46 of the crucible 28 through the bolt 44 and the attachment bed for the crucible 43; another system energizes the support 50 from the brush frame 95a through the brush 99a, the electrode disc 36a and the hollow shaft pipe for the torch part 53, and further energizes the electrode rod 46a within the hood 52 from the support 50.

Argon gas is fed from the gas piping fixture 56 to the hollow shaft pipe for the torch part 53, passing through the support 50 and the arm 51 to the hood 52 where the argon gas is blown out toward the crucible in such a way as it may surround the electrode rod 46a.

In the initially set condition as described above, the first arc starting-up is conducted by a general type of arc generating apparatus (not indicated in the drawings), and arc is generated between the electrode rods 46 and 46a to carry out heating and melting of metal 108.

When metal melting is nearly completed, the handle shaft 65 is rotated by a fixed angle, for example 90°, to drive the motor 19 to operate by rotation of the cam 66 of the control shaft 67 as hereinbefore described, thus rotating the small gear 20, rotating gear 18 and the rotating member for the mold 1, and causing the mold 2 to spin around the crucible 28 at a fixed rate. Since the balance weight 3 is opposed to the mold 2, the rotating member for the mold 1 is rotated smoothly and without violent rocking, whereas the rotating member for the crucible 27 is securely retained in the standstill condition because the brushes 99 and 99a are adequately fitted to the electrode discs 36 and 36a by way of the springs 101 and 101a. A definite magnitude of regular vibration caused by rotation of the rotating member for the mold (1) is transmitted to metal under the melting process in the crucible 28, producing the vibration of the metal.

When melting of metal is completed, the handle shaft 65 with an aim to carrying out casting is rotated further by a fixed angle, for example by 90°, to thus cause the cam 66 of the control shaft 67 to reolve; the cam 66 being an eccentric cam and acting to thrust out the thrusting shaft 75 a fixed distance toward the lever device 76 to cause the top end of the thrusting shaft 75 to contact the top end 79a of the lever 79 under rotation; the lever 79 being instantaneously placed into a slightly counterclockwise revolution centering on the supporting shaft 83 as shown in FIG. 1; the sliding shaft 78 at the supporting shaft 80 being drawn outwardly against the force of the spring 83 to thus bring the top end of the sliding shaft 78 out of engagement with the engaging concave portion 94 of the engaging shaft 85, whereby the inclined sliding surface 93 while being fitted to the top end of the sliding shaft 78 slides, and the engaging shaft 85 is urged by force of the spring 92 to project out by a fixed length out of the upper surface of the annular wall 25; the projected end being fitted to the tapered groove 87 of the saucer 29; and, the engaging shaft 85 revolving as the rotating member for the mold 1 is slidingly rotated along the tapered groove 87 to arrive at the deepest portion 87a of the tapered groove 87 whereby the engaging shaft 85 gets into engagement with the saucer 29, causing the rotating member for the crucible 27 to revolve together with the rotating member for the mold 1 swiftly at a high revolution rate.

At the point of this stage, the crucible 28 with its flow-out portion 28a being opposed to the flow-in portion for metal in the mold 2 is rotated in impact-wise and swiftly to thereby make molten metal in the crucible 28 fly and flow into the mold 2 vigorously by great centrifugal force. In this case, if a crucible having the hood 48 and small chamber 49 formed as shown in the example for embodiment is employed as the crucible 28, the hood 48 prevents molten metal from overflowing out of the crucible 28 even at the time of impact being initially applied, while the small chamber 49 acts to draw and hold therein molten metal which tends to rise along the wall of the crucible 28 due to force of impact and, with its inner surface so shaped as to carry smoothly molten metal to the flow-out opening 28a by means of the impact force, can pour molten metal into the mold 2 without waste and with adequate force.

In case the handle shaft 65 is operated to bring the thrusting shaft 75 in engagement with the concave portion for rotating the crucible 105 of the cam 66, the rotating member for the crucible 27 begins to revolve, whereas in the switching mechanism for electrodes, in contrast, the brushes 99 and 99a are kept fitted resiliently to the electrode discs 36 and 36a. This is due to a very short time lag existing until the thrusting shaft 75 acts on the lever device 75 for engagement between the engaging shaft 85 and the saucer 29. Otherwise or if the brushes 99 and 99a are adapted to get apart from the electrode discs 36 and 36a the moment the thrusting shaft 75 acts on the lever device 76, the rotating member for the crucible 27 will come to be forcedly rotated by the rotating member for the mold 1 under rotation, for example through contacting between the under surface of the saucer 29 and the upper surface of the annular wall 25. So as to prevent such adverse conditions, the brushes 99 are provided with the function of braking produced by the friction against the rotating member for the crucible so that the rotating member for the crucible is designed to remain in standstill condition, until the engagement is completely realized, even if the rotating member for the mold is rotated.

Even if the engagement is completed to cause the rotating member for the crucible 27 to revolve, conseqeuntly, the brushes 99 and 99a are held in fitting with the electrode discs 36 and 36a, continuing to apply the brake, unless the handle shaft 65 is operated. Still, the rotational force of the rotating member for the mold 1 is by far more powerful than it, thus preventing the force of braking from exerting any effect on the rotation of the rotating member for the mold 1 and the one for the crucible 27 after having been engaged.

When the engagement is observed to be completed, the handle shaft 65 is further rotated by a fixed angle, for example by 45°, whereupon the thrusting shaft 75 gets into engagement with the concave portion for actuating the brush to open 106 on the cam 66, while the rotation of the control shaft 67 acts to rotate the switching shaft 70 through the universal coupling 69; and the cams 72 and 72a of the switching shaft 70, allowing their protrusions 107 and 107a to be fitted to the cam fitting portions 100 and 100a of the brush frames 95 and 95a to thereby thrust the cam fitting portions 100 and 100a away to the left and right sides, causes the whole brush frames 95 and 95a to travel outside, thus detaching the brushes 99 and 99a from the electrode discs 36 and 36a.

By this, electric power to the electrode rods 46 and 46a is disconnected, and arc is extinguished. In the gas feeding system as well, movement of the brush frame 95a causes the same 95a to be fitted to the limit switch 102 attached to the base platform for fixing 63 for actuating thus setting the solenoid valve for gas feeding (not shown in the drawings) in the closed position to interrupt the gas feeding to the fixture for gas 56. When one hour has passed after casting of molten metal 108 has been conducted, the handle shaft 65 is restored to the original condition, or a stop button for the motor as not shown in the drawings is pushed to stop the revolution of the motor 19, to thus complete the whole casting process.

If a speed controlling mechanism for a motor such as the generally known ones based on a variable-voltage, -current or -resistance control is provided in the casting apparatus according to the present invention so as to change the speed of the motor 19, furthermore, it can conveniently regulate the initial rotation rate at which the rotating member for the crucible 27, getting into engagement with the rotating member for the mold 1 under rotation driven by the motor 19, starts to revolve in impact-wise. That is to say; when the initial rotation for the rotating member for the crucible 27 is too vigorously high because of too large a number of revolutions of the motor 19, molten metal in the crucible 28, due to the impact force produced on the occasion of engagement, gets possibly overflown out of the crucible 28, counter-flown to the outside through the flow-in portion of the mold, or comes to peel off the refractory membrane formed by coating on the inner surface of the mold; therefore, feasible with such a speed controlling mechanism for a motor is a mode of operation capable of realizing at the time of engagement such a number of revolutions as may not give rise to above mentioned problems and increasing for greater centrifugal force for casting after engagement.

As having been hereinbefore mentioned, the present invention comprises a centrifugal casting apparatus capable of functioning to pour molten metal into the mold 2 with adequate force from the very beginning of casting by allowing the mold 2 alone to revolve around the crucible 28 at a fixed speed in advance of melting of metal in the crucible 28, and bringing the crucible 28 into engagement with the mold 2 after completion of melting of metal for rotating swiftly in an impacting manner, and this enables molten metal to be filled under pressure into the mold 2 sufficiently, producing the dense, precisely formed, high-quality products for dentistry.

In addition, metal charged in the crucible 28 is provided with regular vibration of a certain magnitude through rotation of the rotating member for the mold 1, resulting in efficient melting of metal. In other words, heat is better transferred and spread in heating metal being provided with vibration and brought in a dynamic state than when heating metal being at rest, and metal is not locally superheated to an abnormal extent but heated uniformly; in this way, melting of metal can be completed, with the resulting molten metal having a temperature slightly higher than the melting point of the metal.

By means of this, metal is in the uniformly molten state, without being superheated at the part irradiated by the arc, which facilitates and simplifies melting for casting the whole metal in a crucible with the difference in temperature of molten metal between the arc-irradiated and other surrounding portions being retained within 100° C. that has been conventionally regarded as requisite for casting. The resulting molten metal, being freed of abnormally superheated portion, neither exerts any adverse heat effect on the molds nor degrades them, thus yielding cast products free of sintering and with beautiful exterior surface.

The quantity of metal to be molten, conventionally required to amount up to about three times that of the final casting product, can be reduced down to less than two times in accordance with the present invention, as having been confirmed by the following experiment:

That is to say: so as to prepare a partial denture, a casting for dentistry weighing about 10 g as the finished product, 18 g of cobalt-chrome is molten with the use of the apparatus according to the present invention, and cast into a mold heated at 900° C., resulting in a cast product freed of sintering and having beautiful exterior surface. In the conventional centrifugal casting apparatus in which the casting pressure by dead head is utilized, metal equivalent to about three times the quantity of the cast product is required to be molten, whereas in accordance with the present invention, in constrast, greater centrifugal force for casting is adapted to be produced from the very beginning of casting, thus enabling casting to be carried out with the use of a smaller quantity of molten metal.

Referring now to characteristic features of the apparatus according to the present invention, disc-shaped rotating member for the crucible 27, so constructed to be positioned in engagement with rotating member for the mold 1 at its central part, can revolve stably without rocking as the rotating member for the mold 1 is rotated, facilitating smooth casting of molten metal with no decreased force of pouring for casting; and, in employing the apparatus according to the present invention as an argon-arch type as exemplified in the embodiment, hollow shaft pipe for the disc body 34 and hollow shaft pipe for the torch part 53 are placed internally within the hollow shaft pipe for the saucer 30, a support pipe for the rotating member for the crucible 27, whereby the gas and electric systems are able to be unified or put together without leading-in of electric wiring, etc., thus realizing a size reduction of the whole casting apparatus, elimination of troubles in connection with electric wiring, and the like; furthermore, when the rotating member for the crucible and rotating member for the mold are provided in an inclined condition, the frame for the appratus can be reduced in breadth without occupying a larger level area, and the melting state of metal can be observed from the outside easily.

As to the loading and unloading mechanism 62 serving to transmit the rotation of the rotating member for the mold 1 to the rotating member for the crucible 27 for revolving therewith in one piece, a mechanically operable clutch having an engaging claw or an electrically operating magnetic clutch may be utilizable in addition to the one as shown in the embodiment; still, in the embodiment which is so constructed as to achieve assembling to one piece of the two rotating bodies 1 and 27 by operating the handle shaft 65 for actuating the lever device 76 and through engagement function of the engaging shaft, there are conferred several advantages such as functional simplification, size reduction and reduced trouble occurrence inclusive of failures.

In the example of embodiment which comprises a mechanism utilizing the cams 72 and 72a, etc., of enabling operation of one handle shaft 65 to actuate the engaging mechanism above mentioned and switch on and off the supply systems for electricity, gas, etc., a series of operational processes ranging from rotation of the rotating member for the mold 1 to completion of casting can be carried out into practice in a systematized manner by means of the handle shaft 66 alone, facilitating greatly the operation of the apparatus.

What I claim is:

1. A centrifugal casting apparatus for dentistry comprising: a rotatable platform means provided with a major surface and adapted for rotation about an axis normal to said major surface defining the center of rotation of said platform means, said platform means being provided with a cutout portion defining a through hole at the center of rotation; a mold mounted on said major surface radially spaced from said center of rotation; a driving mechanism associated with said platform means for rotating said platform means; a rotating member having an upper surface and an axis of rotation normal to said upper surface and coincident with said axis defining said center of rotation; a crucible mounted on said upper surface and radially displaced from said center of rotation; rotation transmitting means attached to said rotating member and associated with said drive mechanism via said through hole at the center of rotation to transmit rotation of said platform means to said rotating member; means associated with said rotation transmitting means for engaging said rotating member with said rotation transmitting means to impart the rotation of said rotating member after commencement of rotation of said platform means; and means associated with said crucible for melting metal charged into said crucible.

2. A centrifugal casting apparatus for dentistry in accordance with claim 1 including a balance weight mounted on said platform means opposite said mold.

3. A centrifugal casting apparatus for dentistry in accordance with claim 1, wherein said driving mechanism comprises a rotating gear having a through bore at the center thereof in communication with the through hole of said platform means, a motor operatively coupled to said gear, and a hollow shaft pipe having said gear mounted thereon, said hollow shaft pipe being supported on the upper and lower sides thereof by a supporting frame.

4. A centrifugal casting apparatus for dentistry in accordance with claim 1, wherein said driving mechanism includes a disc body having a hole therethrough aligned with the hole through said platform means and a hollow shaft extending through said hole.

5. A centrifugal casting apparatus for dentistry in accordance with claim 1, wherein said rotating member for said crucible includes a disc body mounted on said platform means, said disc body having a hole therethrough aligned with the hole in said surface means, a hollow shaft support means extending through said hole in said disc body, and torch means mounted on said hollow shaft support means, said torch means extending into said crucible, wherein said hollow shaft support means carries gas to said torch means.

6. A centrifugal casting apparatus for dentistry in accordance with claim 1, wherein said rotation transmitting means comprises a groove for engaging the reverse side of said rotating member for the crucible, an engaging shaft positioned adjacent said groove for engagement therewith, said engaging shaft being movably disposed in said platform means to enter into the said groove, and a control shaft for controlling said groove means for movement out of and into said rotating member, said control shaft being operable from outside the apparatus.

7. A centrifugal casting apparatus for dentistry in accordance with claim 5, wherein said groove is positioned on said platform means below said major surface and said groove means includes a tapered portion and a concave portion, said engaging shaft sliding along said tapered portion and then engaging said concave portion.

8. A centrifugal casting apparatus for dentistry in accordance with claim 1, wherein said platform means and said rotating member are inclined with respect to the horizontal.

* * * * *